United States Patent [19]
Flora et al.

[11] Patent Number: 5,491,409
[45] Date of Patent: Feb. 13, 1996

[54] MULTIPLE YOKE EDDY CURRENT TECHNIQUE FOR DETECTION OF SURFACE DEFECTS ON METAL COMPONENTS COVERED WITH MARINE GROWTH

[75] Inventors: John H. Flora; Hubert L. Whaley, both of Lynchburg, Va.

[73] Assignee: The Babcock & Wilcox Company, New Orleans, La.

[21] Appl. No.: 973,515

[22] Filed: Nov. 9, 1992

[51] Int. Cl.$^6$ .......................... G01R 33/12; G01N 27/82
[52] U.S. Cl. .......................... 324/242; 324/235; 324/238
[58] Field of Search .................................. 324/238, 240, 324/241, 242, 232, 262, 226, 235

[56] References Cited

U.S. PATENT DOCUMENTS

| | | | |
|---|---|---|---|
| 3,611,120 | 10/1971 | Forster | 324/241 |
| 3,617,874 | 11/1971 | Forster | 324/232 |
| 3,875,502 | 4/1975 | Neumaier | 324/241 |
| 4,510,447 | 4/1985 | Moyer | 324/225 |
| 4,594,549 | 6/1986 | Smith et al. | 324/242 |
| 4,954,777 | 9/1990 | Klopfer et al. | 324/241 |

FOREIGN PATENT DOCUMENTS

950696 of 1962 United Kingdom.

*Primary Examiner*—Walter E. Snow
*Attorney, Agent, or Firm*—Daniel S. Kalka; Robert J. Edwards

[57] ABSTRACT

Defects such as corrosion located on the exterior of a component such as a metal pipe, tank, vessel or support structure which is insulated by a coating or cover, are detected by a low frequency eddy current (LOFEC) system. A magnetizing yoke in the shape of an inverted U is placed on the cover insulating a metal component. An excitation coil is wrapped around the magnetizing yoke for carrying an altering current in order to produce an alternating magnetic field by the magnetized yoke. The alternating magnetic field produced by the magnetized yoke induces an eddy current which runs through the metal component between the legs of the yoke. A pair of magnetic flux sensors are used in differential connection beneath one or more excitation coils which can be articulated to conform to varying pipe diameter. In addition, an absolute signal response can be obtained from one of the receiver coils. This arrangement allows for the reduction and minimizing of unwanted and extraneous signal responses caused by variations in the component structure while the yoke is scanned about the cover and a positive separation of loss of metal signals (CUI) from artifact signals. Defects located on the surface of pipes or tanks covered with marine growth can be detected using the DPEC probe with either a signal magnetic flux sensor located beneath the excitation coil or a plurality of magnetic flux sensors differentially connected.

18 Claims, 10 Drawing Sheets

MULTIPLE YOKE EDDY CURRENT TECHNIQUE FOR DETECTION OF SURFACE DEFECTS ON METAL COMPONENTS COVERED WITH MARINE GROWTH

BACKGROUND OF THE INVENTION

1. Field of the Invention

The present invention relates, in general, to the detection of corrosion and in particular to a new and useful method and device for detecting corrosion on a component that is covered by various materials while reducing unwanted signals.

2. Description of the Related Art

Corrosion on the exterior of components such as pipes, vessels and support structures is a pervasive problem throughout the petroleum and chemical process industry costing many millions of dollars annually. A majority of these components are covered with material such as insulation which promote the corrosion by entrapment of water at the metal/cover interface. The removal of these covers and coatings for visual inspection is very costly and accounts for a substantial portion of the annual maintenance costs. Some methods have been developed in an effort to inspect covered components without removal of the insulation or covers.

One method developed for the inspection of pipes, tanks, and vessels through insulation is referred to as the Transient Electromagnetic Probe (TEMP). Two relevant patents have been issued; SPIES (U.S. Pat No. 4,843,320) and Lara (U.S. Pat. No. 4,843,319). This method uses the decay time of a diffusing eddy current pulse in the vessel wall to measure its thickness. The basic method is distinctly different from the low frequency eddy current (LOFEC) method in that a transient decay time of diffusing eddy current is measured rather than flux field perturbations caused by a localized defect. Other distinguishing differences are:

1. TEMP measures the average wall thickness over a large ($\geq$16 inches diameter)—LOFEC detects the loss of surface material due to corrosion under insulation (CUI) in areas as small as 1" diameter.
2. TEMP is not a scanning technique—the very large probe head must be left in place for about 3 seconds to make a single measurement. The LOFEC method can be scanned at least as fast as 4–6"/sec (probably faster) continuously producing output signals. Therefore, the LOFEC technique can be used as an inspection, as opposed to a sampling tool.
3. There is no evidence that the TEMP method can handle the significant "artifacts" that produce signal perturbations in electromagnetic testing—these are aluminum cover overlaps, carbon steel retaining wires under the aluminum, circumferential weld beads, hidden taps or plugs, nearby support brackets, steam trace lines, etc. The LOFEC method has been designed to eliminate or minimize the effects of all those artifacts.

A second method which has been developed for the CUI problem is the portable, real-time x-ray system (LIXI®). Low energy x-rays are directed tangentially to the pipe so that they penetrate the insulation but not the pipe wall, thus imaging the corrosion area. This technique is much too slow to be used as an inspection tool to cover long lengths of pipe. The slow speed is due to a very limited field of view and the many tangential shots required to look at just one axial location on the pipe. It would be best suited to do spot checks for confirmation of corrosion damage after detection by a scanning method such as LOFEC. A second serious problem with the portable x-ray method is that scale in the corrosion site may tend to hide the corrosion damage.

In response to the deficiencies found in the methods listed above, a low frequency eddy current (LOFEC) method was developed for detecting corrosion and other defects on the surfaces of metal components that are covered with various materials such as paint, foam rubber, marine growth, calcium silica insulation and relatively thin metal sheets. The object of the LOFEC method is to detect surface defects such as corrosion on the component while leaving the covering material intact.

Figure 1:
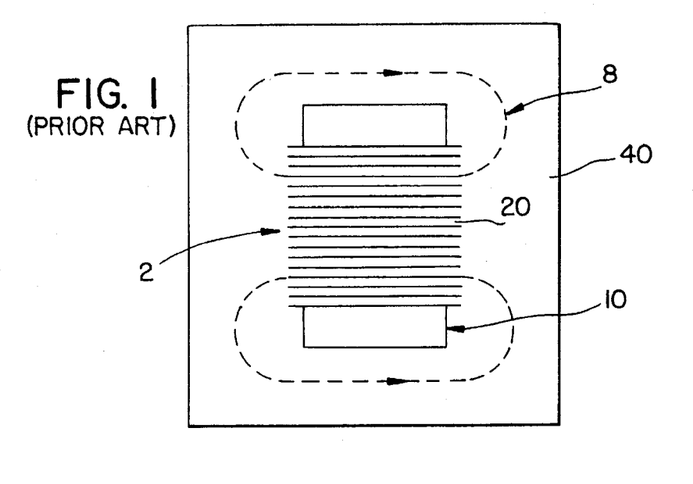
FIG. 1 is a top view of a known probe for a low frequency eddy current system.
Figure 2:
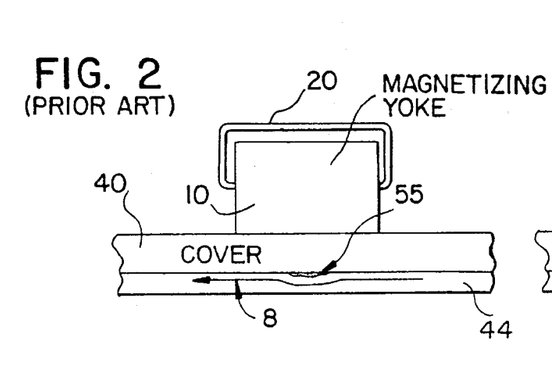
FIG. 2 is a side view of the probe of FIG. 1.

FIGS. 1–5 illustrate a basic LOFEC probe generally designated 2 used for detection of surface defects such as corrosion under insulating covers. The LOFEC probe depicted in FIGS. 1–5 comprises an inverted U-shaped yoke 10 having legs 11 placed on a uniform manufactured cover 40 of a component 44 such as a steel plate. An excitation coil 20 is wound about the magnetizing yoke 10 between the legs 11. An alternating current 4 composed of one or more sinusoidal components is generated and applied to terminals 22 of the excitation coil 20. This alternating current 4 produces an alternating magnetic field 18 in the inverted U-shaped yoke 10. The yoke 10 guides the magnetic field through the cover 40 and into the component 44 beneath. If the component 44 is a ferromagnetic steel, the magnetic field 18 will be concentrated in the plate and directed from one leg of the yoke 10 toward the other. The alternating field 18 induces eddy currents 8 in the steel and other metals, (e.g., aluminum covers), located between the probe and the steel. The induced currents 8 tend to flow between and around the legs 11 of the U-shaped yoke 10 as illustrated in FIG. 1. Both the current 8 and the magnetic flux 18 are concentrated in the materials near and under the yoke 10.

Figure 3:
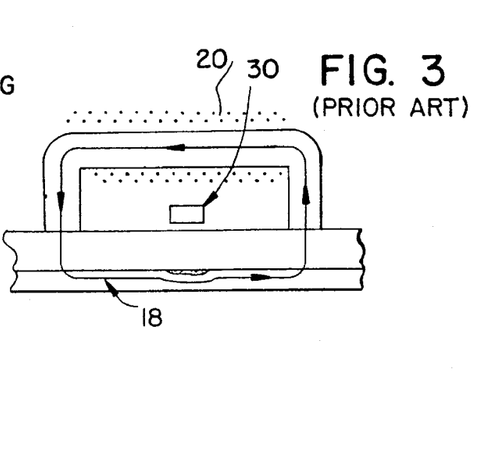
FIG. 3 is a cross-sectional front view of the probe of FIG. 1.
Figure 4:
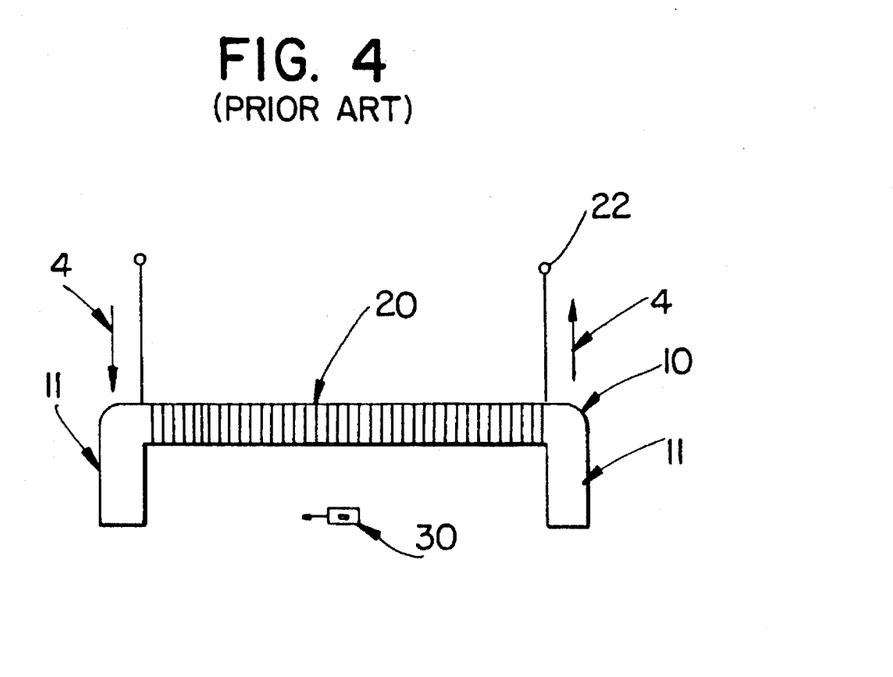
FIG. 4 is a partial front view of the probe of FIG. 1.
Figure 5:
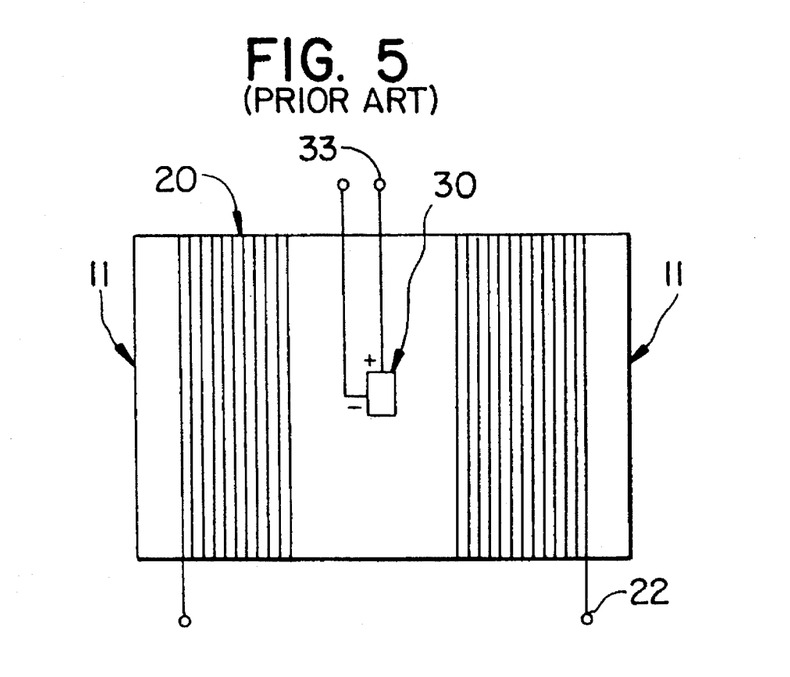
FIG. 5 is a bottom view of the probe of FIG. 1.

FIG. 3 shows that a magnetic flux sensor 30 is located between the legs 11 of the U-shaped magnetizing yoke 10 beneath the excitation coil 20. The sensor 30 lies in a plane passing through the cross-section of the legs 11. The flux sensor 30 is an electronic device, such as a coil of conducting wire or a Hall element semiconductor that provides a signal response voltage proportional to the intensity of the magnetic flux 18 intercepted by the sensor 30 flux. Under normal conditions, e.g., a uniform steel structure with no surface defects, the magnetic flux 18 and induced eddy currents 8 in the region directly under the excitation coil windings 20 are parallel to the plane formed by the sensor 30 that intersects the legs 11. The magnetic flux 18 flows from one leg 11 to the other and induced current 8 flows perpendicular to the flux 18. The presence of a near surface defect 55 in the steel component 44, such as corrosion, causes a change in the magnitude, phase and direction of the induced currents 8 and associated magnetic field 18 within the steel 44 and in the region between the steel 44 and the probe 2.

Surface defects 55 are identified by scanning the probe 2 over the cover 40 of the structure 44 and detecting the signal response voltage, observed at terminals 33 of the flux sensor 30.

However, presently there is no known method or device for reducing or minimizing extraneous and unwanted signal responses caused by variations in the geometry and electromagnetic properties of the component 44 when using the LOFEC technique.

Additionally, no method or device is known which can detect defects on metal components covered with marine growth while minimizing extraneous signal responses.

SUMMARY OF THE INVENTION

The present invention comprises a LOFEC method and device for detecting corrosion on a covered metal component while at the same time minimizing extraneous and unwanted signal responses caused by variations in the properties of the component. The present invention can also be used to detect the presence of defects such as corrosion on metal components covered with marine growth.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 6:
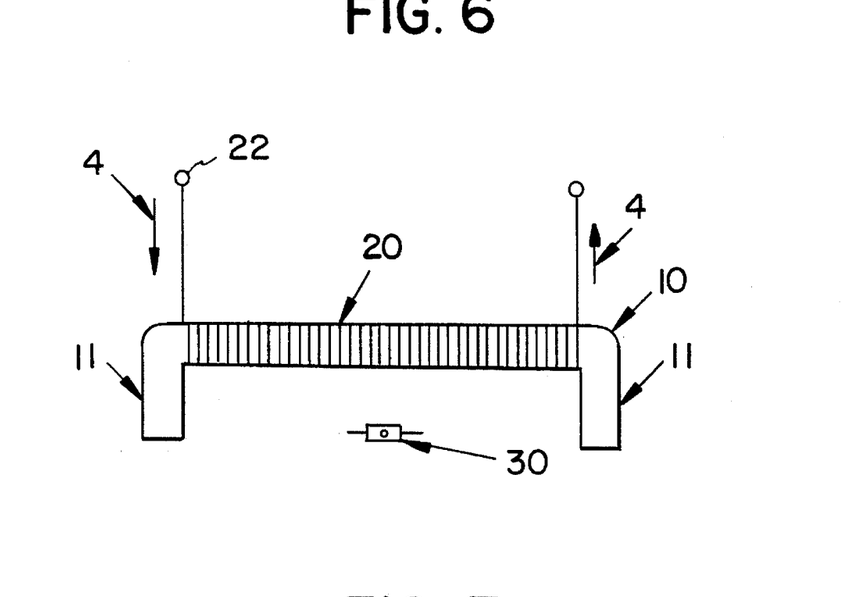
FIG. 6 is a partial elevated front view of a probe of the present invention.
Figure 7:
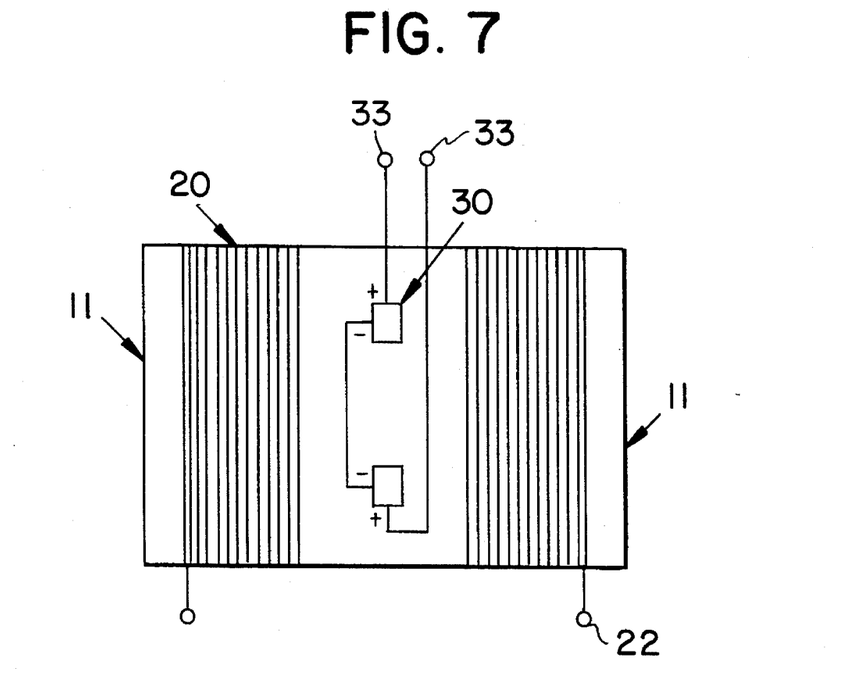
FIG. 7 is a bottom view of the present invention shown in FIG. 6.

Referring to FIGS. 6 and 7, the present invention embodied therein comprises a deep penetration eddy current (DPEC) system having a magnetizing yoke 10 of the inverted U-shaped design with legs 11 and wrapped by excitation coil 20 for carrying a current 4 and for ultimately producing a magnetic flux while being moved along the surface of a cover of a metal component for scanning and detecting corrosion on the metal component. Throughout the drawings, the same reference numerals are used to designate the same or functionally similar parts.

As illustrated in FIG. 7, a plurality of magnetic flux sensors 30 are used beneath the excitation coil 20 in concert in order to detect perturbations in the magnetic flux caused by defects in the surface of the steel component, while at the same time providing for a reduction and minimization of unwanted and extraneous signal responses caused by variations in the structure of the components which is being inspected.

FIG. 7 shows that two magnetic flux sensors 30 are located and centered beneath the excitation coil 20. The sensors 30 are oriented such that a magnetic flux component that is upward and parallel to the center axis of both sensors 30 produces a positive signal from one sensor and a negative signal from the other sensor.

This result can be achieved through a winding of one sensor coil in the clockwise direction and the other sensor coil in the counter-clockwise direction.

The sensors 30 are then connected in series opposing so that signal responses to a common magnetic flux will subtract. By using this arrangement, perturbations in the magnetic flux caused by overlapping ends of aluminum covers and uniform steel wire used for securing the insulation or cover to the pipes will result in a much smaller signal response.

Figure 8:
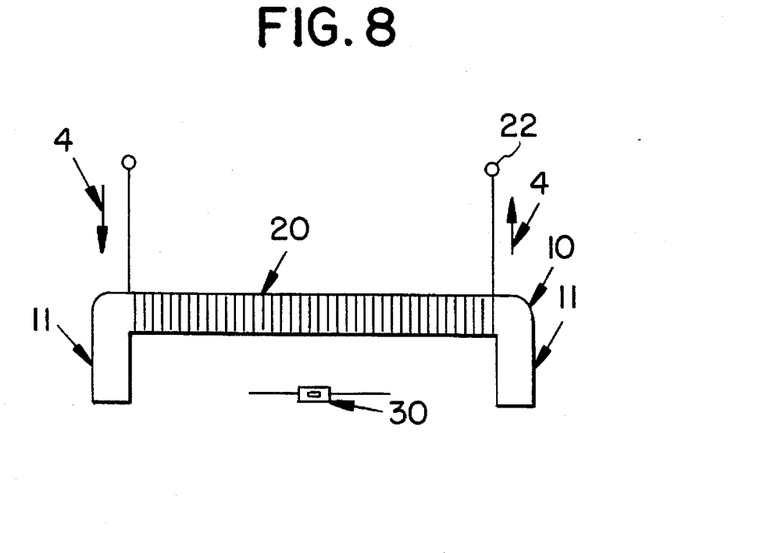
FIG. 8 is a partial front view of a second embodiment of the present invention.
Figure 9:
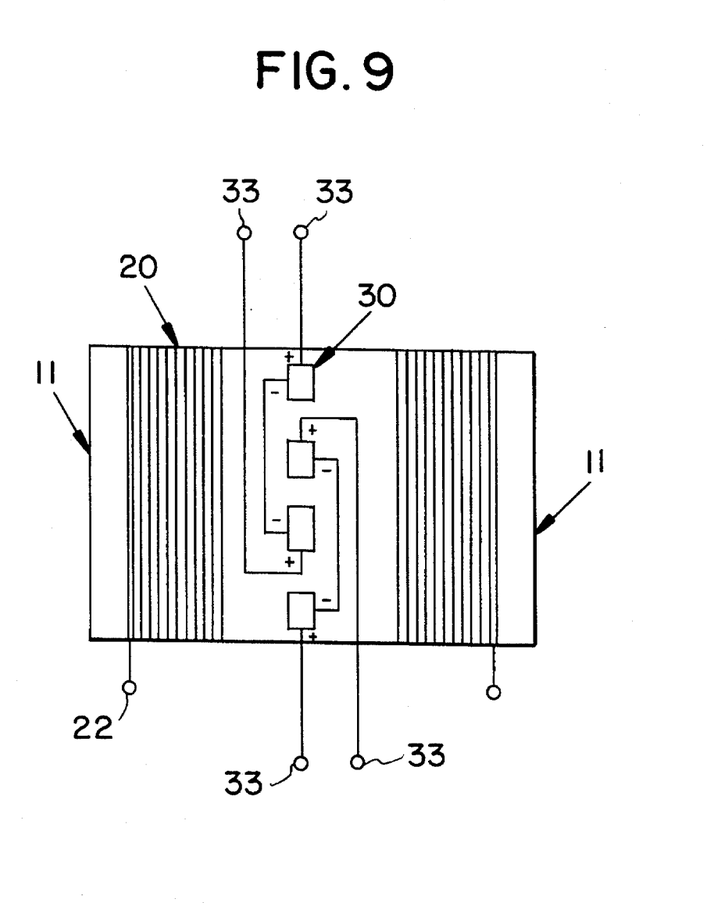
FIG. 9 is a bottom view of the present invention according to FIG. 8.

FIGS. 8 and 9 illustrate that two separate differential connections of sensors 30 are employed beneath the excitation coil 20.

Figure 10:
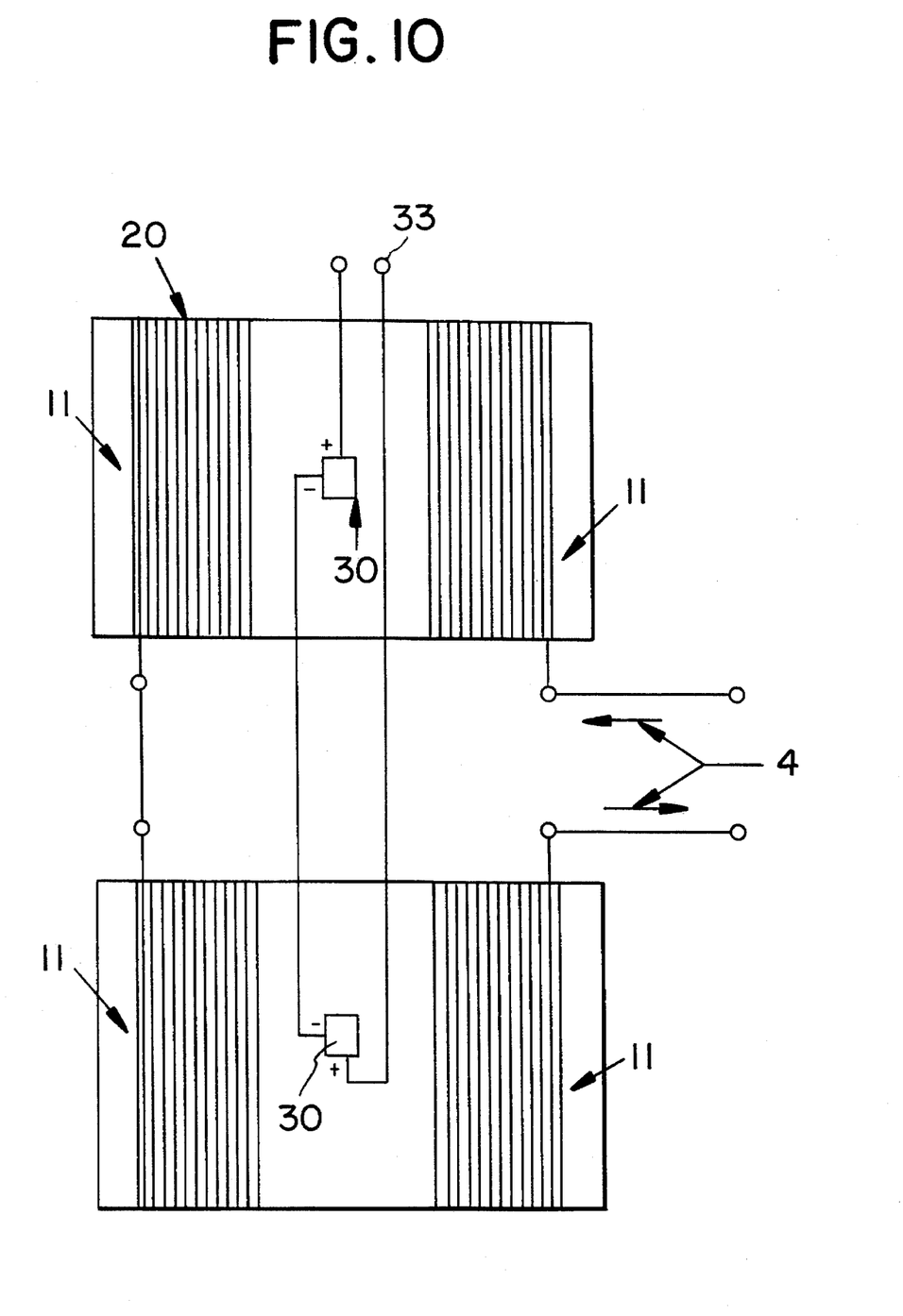
FIG. 10 is a bottom view of a third embodiment of the present invention.

FIG. 10 illustrates the present invention comprising a plurality of magnetizing yokes 10 having excitation coils 20. The magnetic flux sensor 30 is provided beneath each excitation coil 20 and is arranged in differential connection between a corresponding magnetic flux sensor 30.

The configuration illustrated in FIG. 10 is critical to the CUI application. By having two or more separate elements (each comprised of a driver coil and a receiver coil), a differential response (which is necessary to reduce the effects if artifact signals such as overlaps, wires, and circumferential weld beads) can be obtained while permitting the probe to articulate to fit the contour of pipes of varying diameters.

In addition, one of the receiver coils is used to obtain an "absolute" (as opposed to "differential") response. The direction and magnitude of the absolute signal can be used to determine whether signal sources are due to metal loss (i.e., CUI) or added metal (wires, taps, weld beads, etc.). This determination is based on the fact that the absolute signal response will have opposite polarity.

Figure 11:
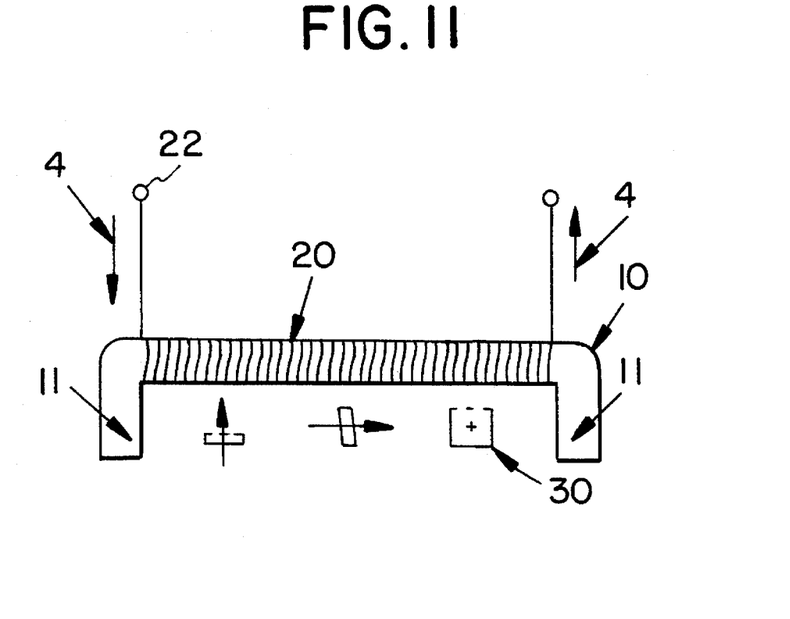
FIG. 11 is a partial front view illustrating the orientation of the magnetic flux sensor according to the present invention.
Figure 12:
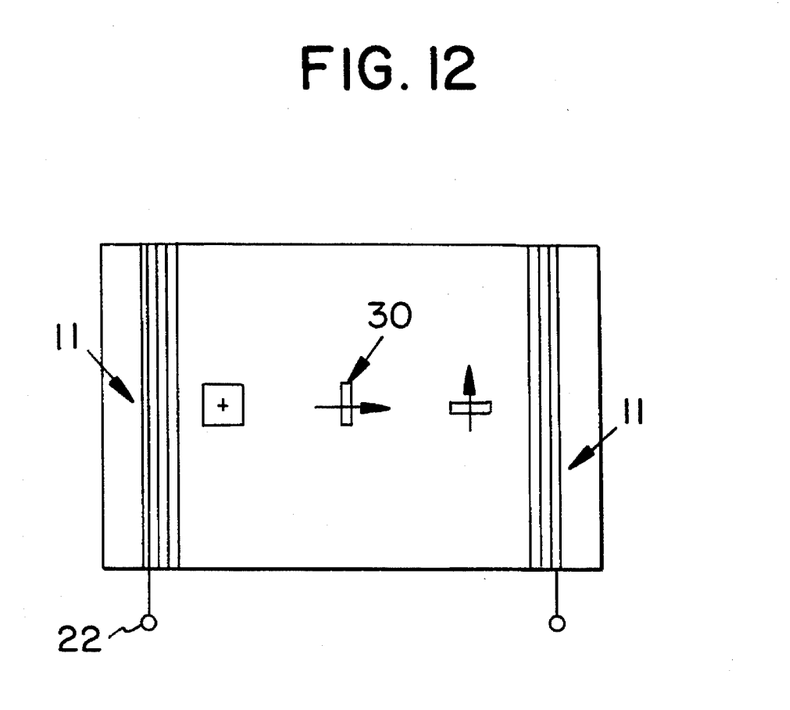
FIG. 12 is a bottom view of the orientation of the magnetic flux sensor according to FIG. 11.

FIGS. 11 and 12 illustrate that magnetic flux sensors 30 are positioned beneath the excitation coil 20 and can be oriented with their axes in one of several directions.

Figure 13:
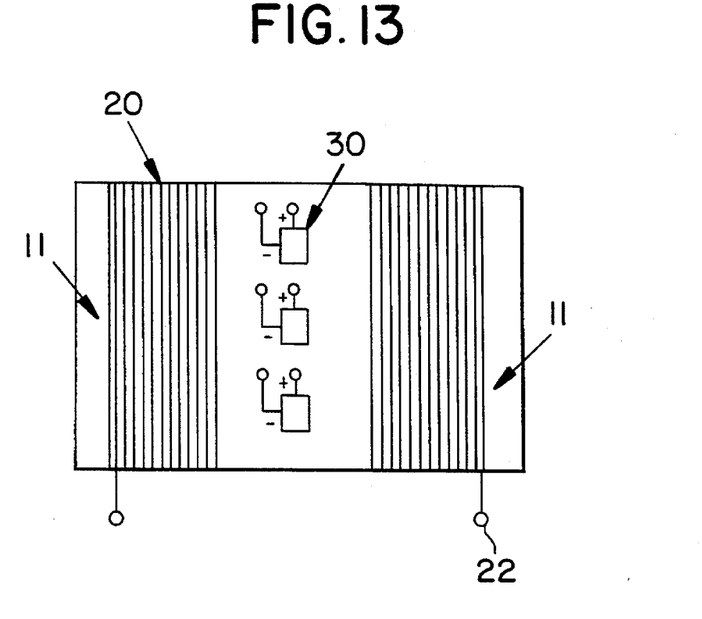
FIG. 13 is a bottom view of a fourth embodiment of the present invention.
Figure 14:
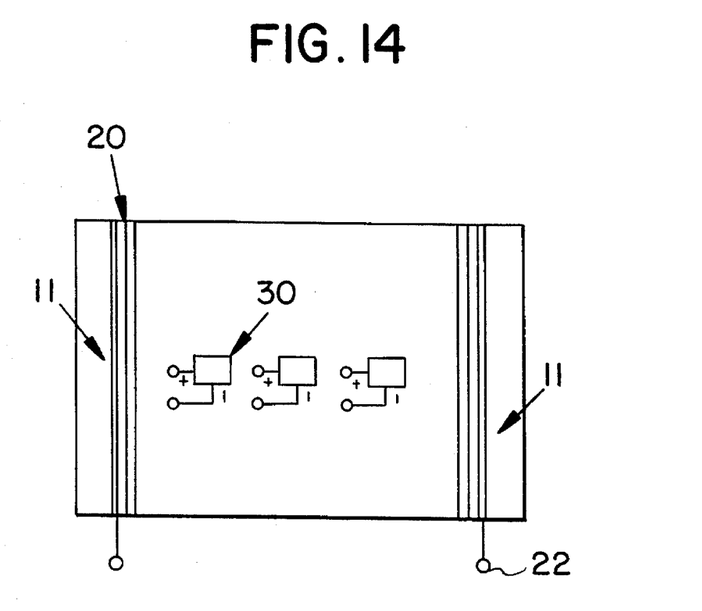
FIG. 14 is a bottom view of a fifth embodiment of the present invention.

FIGS. 13 and 14 show that the magnetic flux sensors 30 in linear arrays are oriented in different directions, either parallel or perpendicular to the excitation coil 20.

Figure 15:
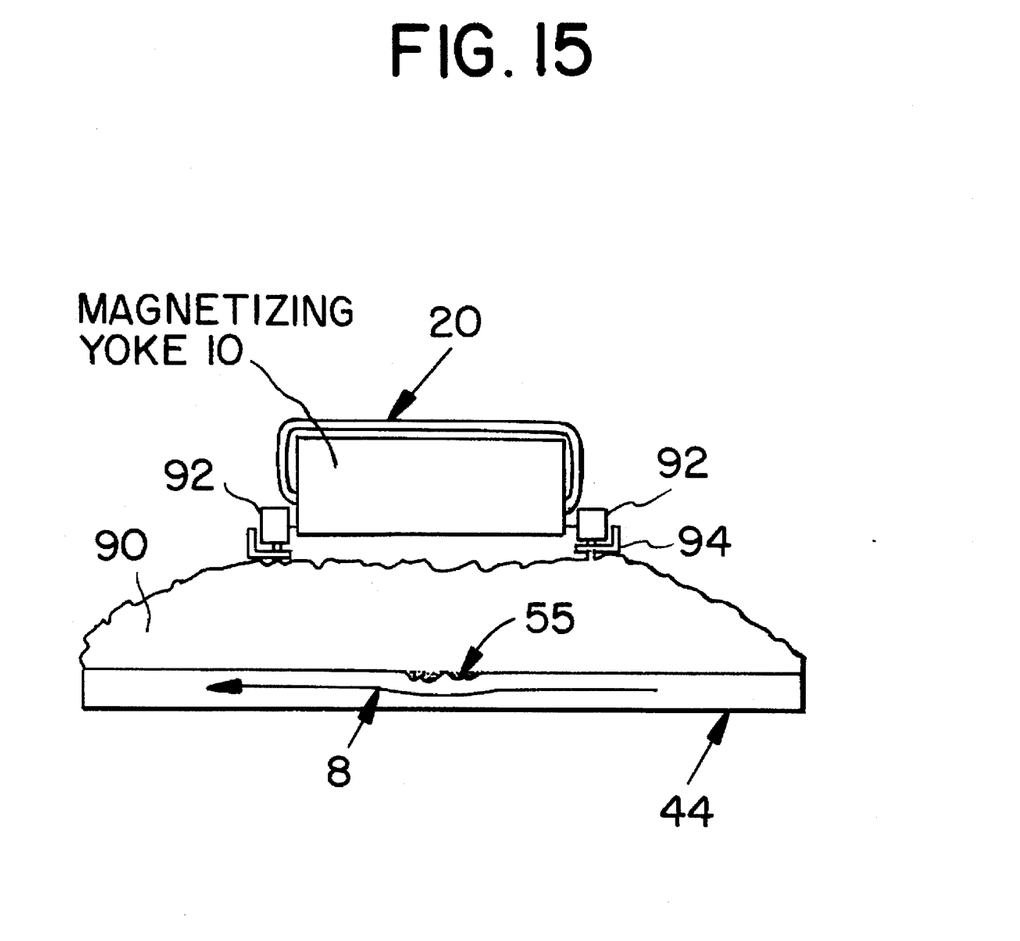
FIG. 15 is a side view of a sixth embodiment of the present invention for detecting defects through marine growth.

FIG. 15 illustrates how the present invention can be used to detect defects on a component such as a metal plate 44 or metal tank encased by irregular marine growth 90 using a magnetizing yoke 10 and excitation coil 20 mounted on wheels or rollers 92 with a track 94. Track 94 includes two angle members or guide rails positioned either vertically or horizontally to allow the wheels 92 to freely roll while simultaneously scanning in a given direction. In detecting defects such as corrosion 55 engulfed by the marine growth 90, a flux sensor 30 can be used by itself or in differential connection with other flux sensors 30, as illustrated in FIG. 7.

Figure 16:
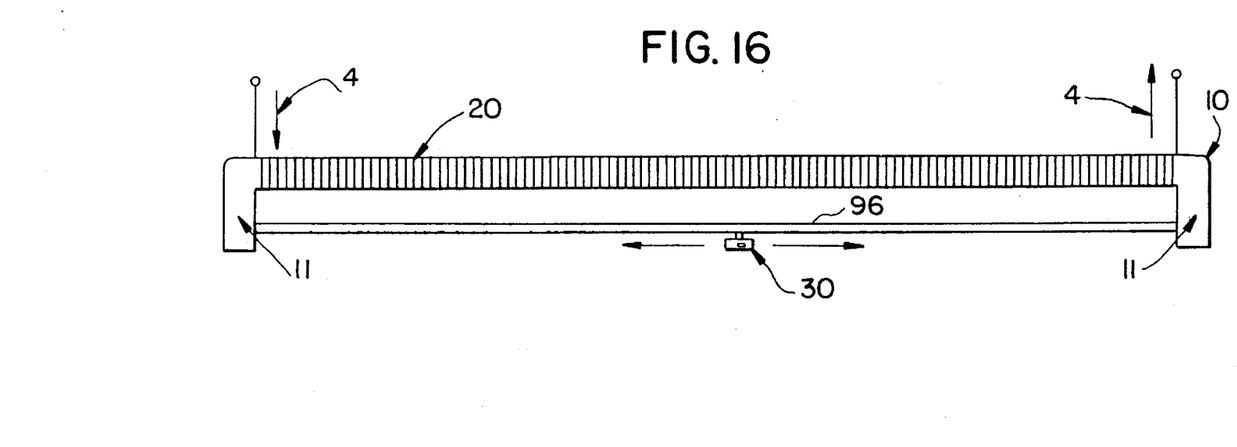
FIG. 16 is a side view of a seventh embodiment of the present invention.
Figure 17:
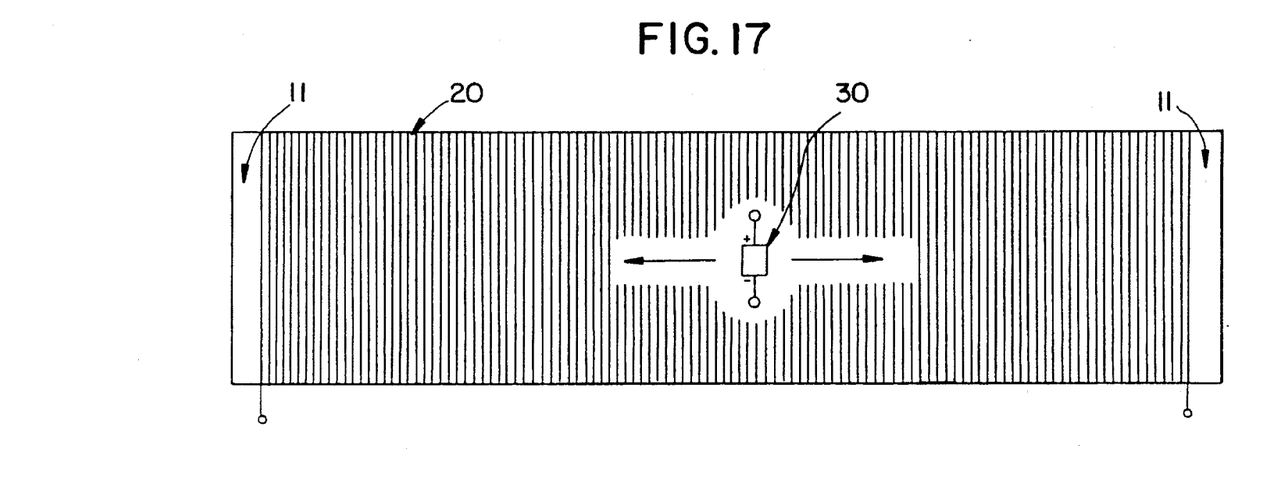
FIG. 17 is a bottom view of the embodiment shown in FIG. 16.

FIGS. 16 and 17 show still another embodiment of the probe in accordance with the present invention. This probe differs from the previous probe configurations in two respects. First, the magnetizing yoke 10 is elongated or enlarged so that the distance between the legs 11 of the yoke 10 is increased to as much as about four or five feet. Second, the magnetic flux sensor(s) 30 are scanned while the magnetic flux sensor 30 in the scan direction indicated by the arrows in FIG. 17. Suitable scanning means 96 includes stepper motors capable of moving sensor 30 which may be automatic or manually controlled.

Figure 18:
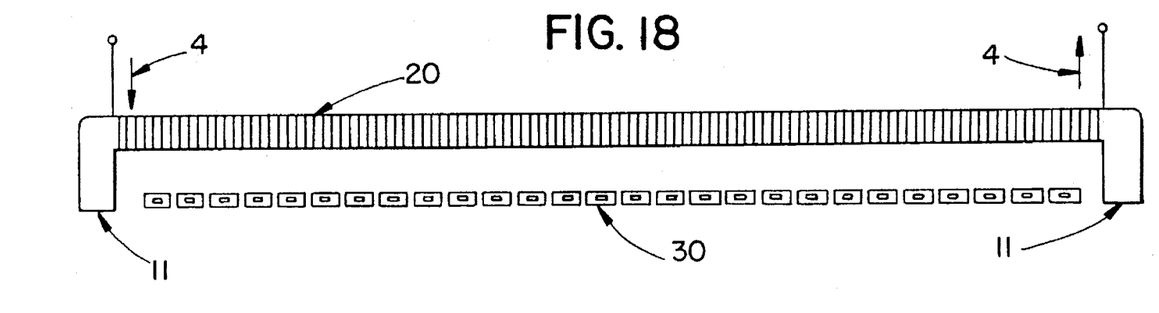
FIG. 18 is a side view of an eighth embodiment of the present invention.
Figure 19:
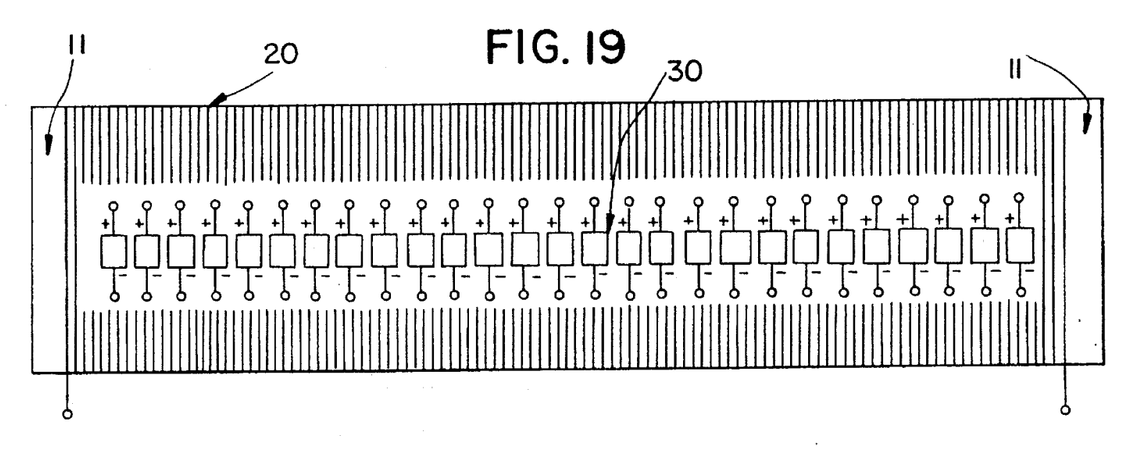
FIG. 19 is a bottom view of the embodiment shown in FIG. 18.

FIGS. 18 and 19 show yet another embodiment similar to FIGS. 16 and 17, but there is a fixed array of sensors 30 that are multiplexed to scan the component. The fixed array of sensors provides the advantages of reduced size, weight and the elimination of moving parts. Inspection of a relatively large area can be accomplished by simply holding the magnetizing yoke 10 against the component and performing the automatic multiplexing and signal response sampling of the sensor array. Advantages of the embodiments shown in FIGS. 16–19 include the following.

The probe detects corrosion on the near surface of components without removing coatings and covers of various materials.

The embodiment of FIGS. 18 and 19 provides a reduction in the size and weight of the scanning mechanism compared to that required to scan both the magnetizing yoke and sensor as a unit over a component.

Stationary magnetic flux sensors in arrays extending from one leg of the magnetizing yoke to the other can be sampled in sequence by using multiplexers to detect the changes in magnetic flux caused by defects in the component, thereby eliminating the requirement for moving parts to inspect the component.

Two or more probes can be aligned side-by-side and parallel to each other to cover larger rectangular areas on the cylindrical surfaces of pipes and tanks with one simple attachment of the probe configuration to the surface of the test component, thereby reducing the time and cost for inspection.

This probe design containing a fixed array of magnetic flux sensors allows a means for sensors, associated electrical cables and on-probe electronics to be sealed for use under water.

Signal responses caused by variables other than defects in the surface of the covered component can be reduced further by multifrequency mixing. The LOFEC instrumentation is programmed to generate excitation currents composed of two or more sinusoidal components. Signal responses for each of these components are detected and applied to a formula having the general form described by the equation:

$$P=F[S(1), S(2), \ldots S(n)] \quad (1)$$

where the value of P predicts the presence of a surface defect or some characteristic of the defects such as depth or length.

The terms $S(1)$, $S(2)$, ... $S(n)$ are the signal responses associated with each sinusoidal frequency component.

The function $F[S(1), S(2), \ldots S(n)]$ in general can take various forms using first, second, third, etc., powers of the terms $S(1)$, $S(2)$ ... $S(n)$.

For example, the signal responses to dents and overlaps in aluminum covers encountered while looking for corrosion on steel pipes, can be reduced by the predictive formula described in the equation below:

$$P(corrosion)=K(1) \times S(1) - K(2) \times S(2) \quad (2)$$

where $S(1)$ is the signal response for a low frequency component, e.g. 20 HZ, and $S(2)$ is the signal response for a significantly higher frequency component, e.g., 160 HZ. $K(1)$ and $K(2)$ are weighing coefficients.

Since the high frequency excitation fields and induced eddy currents are concentrated in thin aluminum covers near the probe, subtraction of the weighted signal response $S(2)$ from the weighted signal response $S(1)$ reduces the signal caused by overlaps and dents in the aluminum covers.

There are several advantages of the present invention as listed below.

First, the invention provides a means for generating magnetic fields that penetrate through covers and coatings, such as insulation and aluminum sheets, to detect defects on the near surface of ferromagnetic components, such as steel pipes and tanks.

Second, the size and shape of the magnetic yoke and excitation coil provide for increased penetration of the time changing magnetic fields and associated eddy currents that are induced in the ferromagnetic components under interrogation.

Third, location of the magnetic flux sensing coil in the space under the excitation coil and between the legs of the magnetizing yoke provides a means for detecting changes in the direction, amplitude and phase of the induced eddy current and associated magnetic fields in the vicinity of a defect.

Fourth, the use of pairs of sensors electronically connected in differential pairs provides a means of reducing unwanted signals response caused by variations in the geometry and electromagnetic properties of the component.

While the specific embodiments of the invention have been shown and described in detail to illustrate the application of the principles of the invention, it will be understood that the invention may be embodied otherwise without departing from such principles.

What is claimed is:

1. A method of detecting a defect on a metal component having a cover, the method comprising the steps of:

winding at least one excitation coil around at least two magnetic U-shaped yokes;

placing a magnetic flux sensor underneath each U-shaped yoke, each magnetic flux sensor being differentially connected with respect to each other;

placing the at least two U-shaped yokes of ferromagnetic material on the cover over the component;

applying an alternating current to each excitation coil for producing an alternating magnetic field through each U-shaped yoke thereby inducing eddy currents in the component parallel to a plane formed by said magnetic flux sensor underneath each U-shaped yoke, both the alternating magnetic field and the eddy current having a magnitude, a phase and a direction;

moving the at least two U-shaped yokes along the cover of the component thereby scanning for defects; and monitoring the alternating magnetic field and the eddy current using the sensors, for changes in at least one of the magnitude, the phase and direction which is indicative of defects on the component.

2. The method according to claim 1, wherein a plurality of pairs of magnetic flux sensors differentially connected with respect to each other are placed in the area between the excitation coil of each U-shaped yoke and the cover of the component.

3. The method according to claim 2, wherein the magnetic flux sensors differentially connected with respect to each other are oriented in a plurality of directions.

4. The method according to claim 2, wherein each magnetic flux sensor is oriented in the same direction.

5. The method according to claim 1, wherein a plurality of U-shaped yokes are placed on the cover of the component.

6. The method according to claim 5, wherein the plurality of yokes are constructed to articulate with varying pipe diameters while still obtaining both a differential and an absolute response.

7. A method of detecting a defect on a metal component coated with irregular marine growth, the method comprising the steps of:
   winding an excitation coil around at least two magnetic U-shaped yokes;
   placing a magnetic flux sensor underneath each U-shaped yoke, each magnetic flux sensor being differentially connected with respect to each other;
   placing each magnetizing U-shaped yoke on the marine growth over the component;
   applying an alternating current to the excitation coil for producing an alternating magnetic field through each yoke thereby inducing an eddy current in the component parallel to a plane formed by said magnetic flux sensor underneath each U-shaped yoke, both the alternating magnetic field and the eddy current having a magnitude, a phase and a direction;
   moving the at least two U-shaped yokes along the cover of the component for scanning for defects; and
   monitoring the alternating magnetic field and the eddy current by the sensor for changes in at least one of the magnitude, the phase and the direction.

8. The method according to claim 7, wherein the magnetic flux sensors differentially connected with respect to each other are oriented in a plurality of directions.

9. The method according to claim 7, wherein each magnetic flux sensor is oriented in the same direction.

10. The method according to claim 7, wherein a plurality of U-shaped yokes are placed on the marine growth of the component.

11. The method according to claim 10, wherein the plurality of U-shaped yokes are constructed to articulate to accommodate varying pipe diameters while still obtaining both a differential and an absolute response.

12. A device for detecting a defect on a metal component having a cover, the device comprising:
   at least two magnetizing U-shaped yokes, each U-shaped yoke having a body supported by at least two legs, the legs for contacting the cover and supporting the body over the cover such that when the U-shaped yoke is placed on the cover of the component, a space is formed between the body, the legs and the cover, each U-shaped yoke being moveable about the cover;
   an excitation coil wound around the body of each U-shaped yoke between the legs for receiving an alternating current and producing an alternating magnetic field through each U-shaped yoke thereby inducing an eddy current in the component parallel to a plane formed by said magnetic flux sensor underneath each U-shaped probe, the alternating magnetic field and the eddy current having a magnitude, a phase and a direction; and
   at least one magnetic flux sensor located within the space of each U-shaped yoke, each of said magnetic flux sensors being differentially connected to another, said sensors detecting changes in the magnitude, the phase and the direction of the alternating magnetic field and the eddy current.

13. The device according to claim 12, wherein a plurality of pairs of magnetic flux sensors differentially connected with respect to each other are located within the space.

14. The device according to claim 12 wherein a pair of magnetic flux sensors differentially connected with respect to each other are oriented in a plurality of directions.

15. The device according to claim 12, wherein a plurality of magnetic flux sensors are located within the space.

16. The device according to claim 12, wherein each magnetic flux sensor is oriented in the same direction.

17. The device according to claim 12, wherein a plurality of magnetizing U-shaped yokes are used on the cover of the component.

18. The device according to claim 12, wherein the plurality of U-shaped yokes are constructed to articulate with varying pipe diameters while still obtaining both a differential and an absolute response.

* * * * *